United States Patent [19]

Kulpe et al.

[11] Patent Number: 5,331,084
[45] Date of Patent: Jul. 19, 1994

[54] FLUORINE-SUBSTITUTED EPOXIDES AND A METHOD FOR THEIR PREPARATION

[75] Inventors: Jürgen Kulpe; Heinz Strutz, both of Frankfurt am Main, Fed. Rep. of Germany

[73] Assignee: Hoechst Aktiengesellschaft, Frankfurt am Main, Fed. Rep. of Germany

[21] Appl. No.: 16,901

[22] Filed: Feb. 12, 1993

[30] Foreign Application Priority Data

Feb. 29, 1992 [DE] Fed. Rep. of Germany ....... 4206387

[51] Int. Cl.$^5$ ............... C07D 301/14; C07D 301/19; C07D 303/04; C07D 303/06
[52] U.S. Cl. ................... 528/402; 549/525; 549/529; 549/536; 549/538; 549/545
[58] Field of Search ............ 549/545, 525, 529, 536, 549/538; 528/402

[56] References Cited

U.S. PATENT DOCUMENTS

| | | | |
|---|---|---|---|
| 3,238,227 | 3/1966 | Tinsley et al. | 549/545 |
| 3,631,972 | 12/1971 | Sheng et al. | 260/348.5 L |
| 5,166,371 | 11/1992 | Shum et al. | 549/529 |

OTHER PUBLICATIONS

Chemical Abstract 118(26): 265354e.
Chemical Abstract 109(23):211217h.
Chemical Abstract 105(10):79866e.
Chemical Abstract 104(6):43196b.
Chemical Abstract 110(9):74879e.

G. Dittus, Methoden der Organischem Chemie, (1965), pp. 385–402.
J. Neurochem., 57:509–519, (1991).
McBee, E.T., et al., *J. Am. Soc. Soc.* 77:915–919 (1955).
Smart, B.E, *J. Org. Chem.* 38:2027–2042 (1973).

*Primary Examiner*—Frederick Krass
*Attorney, Agent, or Firm*—Connolly & Hutz

[57] ABSTRACT

Fluorine-substituted epoxides of the formula

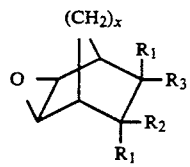

in which the substituents $R_1$ to $R_4$, independently of one another, have the following meanings:

$R_1$ to $R_4$=H, fluorine, $C_1$- to $C_{18}$-alkyl in which some or all of the hydrogens may be substituted by fluorine, and at least one of the substituents $R_1$ to $R_4$ is a completely fluorinated alkyl or an alkyl of the formula

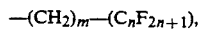

$$-(CH_2)_m-(C_nF_{2n+1}),$$

in which m is 1 or 2, and n is an integer from 1 to 17, and x is 0 or 1.

Furthermore, a method for the preparation of fluorine-substituted epoxides is described.

7 Claims, No Drawings

FLUORINE-SUBSTITUTED EPOXIDES AND A METHOD FOR THEIR PREPARATION

The present invention relates to fluorine-substituted epoxides of the formula

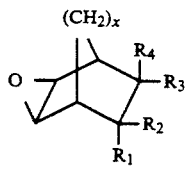

in which the substituents R₁ to R4, independently of one another, have the following meanings:

R₁ to R₄=H, fluorine, C₁- to C₁₈-alkyl in which some or all of the hydrogens may be substituted by fluorine, and at least one of the substituents R₁ to R₄ is a completely fluorinated alkyl or an alkyl of the formula

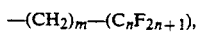

in which m is 1 or 2 and n is an integer from 1 to 17, and x is 0 or 1, and a method for their preparation.

From the wide range of possible fluorine-substituted epoxides, the following compounds are of particular interest:

a) 2,3-epoxy-5,5-bis(trifluoromethyl)bicyclo[2.2.1]heptane,

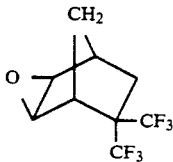

b) 2,3-epoxy-5,6,6-trifluoro-5-(trifluoromethyl)bicyclo[2.2.1]heptane,

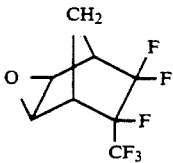

c) 2,3-epoxy-5-(perfluorohexyl)bicyclo[2.2.1]heptane,

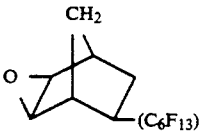

d) 2,3-epoxy-5-(perfluorooctyl)bicyclo[2.2.1]heptane,

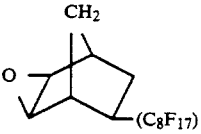

e) 1,2-epoxy-4-(perfluorohexyl)cyclohexane,

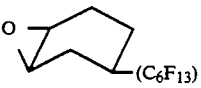

f) 2,3-epoxy-5-(2,2,3,3,4,4,5,5,6,6,7,7,7-tridecafluoroheptyl)bicyclo[2.2.1]heptane,

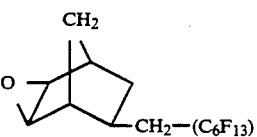

g) 2,3-epoxy-5-(3,3,4,4,5,5,6,6,7,7,8,8,8-tridecafluorooctyl)bicyclo[2.2.1]heptane

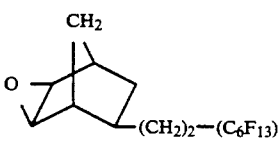

The starting materials for the preparation of fluorine-substituted epoxides are the reaction products of butadiene or cyclopentadiene with a fluorine-substituted alkene. The reaction of butadiene or cyclopentadiene with olefins is described in the literature as a "Diels-Alder reaction". J. Am. Chem. Soc. (1955), Vol. 77, 915-919 and J. Org. Chem. (1973), Vol. 38, No. 11, 2027-2042 describe methods for the preparation of bicyclo[2.2.1]heptene derivatives which contain fluorine and which are suitable starting materials for the preparation of the fluorine-substituted epoxides.

The method according to the invention for the preparation of fluorine-substituted epoxides from the reaction product of butadiene or cyclopentadiene with a fluorine-substituted alkene according to the procedure of a Diels-Alder reaction comprises dissolving the reaction product in dry organic solvent, adding to this solution at normal temperature an organic peroxide in an amount from 1 equivalent to 3 times the equivalent, based on the reaction product, reacting the mixture at temperatures between 40° and 120° C. over an interval from 5 to 50 hours, then distilling off the low-boiling components under reduced pressure, and subsequently purifying the fluorine-substituted epoxide.

The method according to the invention for the preparation of fluorine-substituted epoxides may optionally and preferably be carried out in such a way that 1) the organic peroxide added is peroxyacetic acid or t-butyl hydroperoxide, with molybdenum acetylacetonate as a catalyst,
2) the dry organic solvent used is methylene chloride, benzene, xylene or toluene, in an amount from 100 to 1000 g, based on 100 g of reaction product,
3) the organic peroxide is added as a 0.2 to 5 molar organic solution,
4) the fluorine-substituted epoxide is purified, after removal of the low-boiling components, by distillation under reduced pressure,
5) the fluorine-substituted epoxide, after removal of the low-boiling components, is chromatographed on silica gel, and the mobile solvent used is a mixture of hexane/methylene chloride/diethyl ether (10:10:0.5 parts by volume).

The fluorine-substituted epoxides according to the invention can be used for the preparation of polyethers or polyglycols.

Molybdenum acetylacetonate was obtained from Aldrich Chemie GmbH & Co. KG, 7924 Steinheim.

The method of preparation chosen for the Diels-Alder reaction product produces an isomer mixture of exo- and endo-addition products. It is however also possible to use the pure exo- or endo-addition products of a Diels-Alder reaction as the starting material for the preparation of fluorine-substituted epoxides.

EXAMPLE A

Diels-Alder reaction

Diels-Alder reaction product

All autoclave is charged with 554 ml=884 g (2.5 mol) of perfluorohexylethene, 165 g ( 2.5 mol ) of freshly distilled cyclopentadiene and 5 g of hydroquinone. The autoclave is purged twice with nitrogen. It is then pressurized to 5 bar with nitrogen and heated to 170° C. After 72 hours, the mixture is allowed to cool down, the excess nitrogen pressure is vented, and the autoclave contents are filtered into a distillation flask. The fractional distillation under reduced pressure gives 783 g of the Diels-Alder product with a boiling point of 33° to 35° C. at a pressure of 0.25 mm Hg.

An endo/exo isomer ratio of 77:23 was determined by $^1$H NMR spectroscopy.

The following Examples are intended to explain the preparation of the compounds according to the invention.

EXAMPLE 1

Preparation of 2,3-epoxy-5,5-bis(trifluoromethyl)bicyclo-[2.2.1]heptane 11.5 g (50 mmol) of the Diels-Alder reaction product of 3,3,3-trifluoro-2-trifluoromethyl-1-propene andcyclopentadiene are mixed in 10 ml of dry toluene with 326 mg (1 mmol) of molybdenum acetylacetonate, and 21 ml of a 2.9 molar solution of t-butyl hydroperoxide in toluene (61 mmol) is added dropwise at 22° C. within 30 minutes. During this period, the temperature rises to 45° C. The solution is then heated to 60° C., and after two and a half hours 3 g of molecular sieve 4 A and another 5 ml of the 2.9 molar solution of t-butyl hydroperoxide in toluene are added. After 20 hours of reaction time, the solvent, t-butanol and any remaining t-butyl hydroperoxide are carefully stripped off under reduced pressure. The residue is chromatographed on 160 g of silica gel. The mobile solvent used is a mixture of hexane/-methylene chloride/diethyl ether (10:10:0.5 parts by volume). The product-containing fractions are combined and subjected to fractional distillation under reduced pressure. The product distils at a pressure of 150 to 190 mbar and a temperature of 100° to 124° C.

Yield: 7.94 g=64% of theory
Elementary analysis:

|  | C | H | F |
| --- | --- | --- | --- |
| calc. | 43.9 | 3.3 | 46.3 |
| obs. | 44.5 | 3.4 | 45.5 |

EXAMPLE 2

Preparation of 2,3-epoxy-5,6,6-trifluoro-5-(trifluoromethyl)bicyclo[2.2.1]heptane 8.6 g (40 mmol) of the Diels-Alder reaction product of hexafluoropropene and cyclopentadiene are mixed in 20 ml of dry methylene chloride with 97 ml (80 mmol) of a 0.83 molar solution of peroxyacetic acid in methylene chloride, and the mixture is stirred for 96 hours at room temperature. The low-boiling components are then distilled off under reduced pressure. The residue is washed with two 20 ml portions of water, and the organic phase is dried with magnesium sulfate. The product distils at a pressure of 100 mbar and a boiling point of 60° to 65° C. In order to increase product purity, the distillation is repeated.

Yield: 2.81 g=30% of theory
Identification is by means of gas chromatography with mass-selective detection: M+ =232.

EXAMPLE 3

Preparation of 2,3-epoxy-5-(perfluorohexyl)bicyclo[2.2.1]heptane 103 g (250 mmol) of the Diels-Alder reaction product of 3,3,4,4,5,5,6,6,7,7,8,8,8-tridecafluoro-1-octene (perfluorohexylethene) and cyclopentadiene are mixed in 10 ml of dry toluene with 815 mg (2.5 mmol) of molybdenum acetylacetonate, and 104 ml of a 3.6 molar solution of t-butyl hydroperoxide in toluene (375 mmol) are added dropwise at 25° C. within 50 minutes. During this time, the temperature rises to 45° C. The solution is then held at 60° C. for 24 hours, after which the solvent, t-butanol and any remaining t-butyl hydroperoxide is distilled off in a rotary evaporator under reduced pressure. The residue is filtered over silica gel, followed by washing with two 10 ml portions of toluene. In the course of the distillation over a packed column 15 cm long which is packed with 4 mm glass rings, the product distils at a pressure of 350 mbar and a boiling point of 54° to 56° C.

Yield: 70.0 g=65% of theory

EXAMPLE 4

Preparation of 2,3-epoxy-5-(perfluorooctyl)bicyclo[2.2.1]heptane 128 g (250 mmol) of the Diels-Alder reaction product of 3,3,4,4,5,5,6,6,7,7,8,8,9,9,10,10,10-heptadecafluoro-1-decene (perfluorooctylethene) and cyclopentadiene are mixed in 10 ml of dry toluene with 815 mg (2.5 mmol) of molybdenum acetylacetonate, and 104 ml of a 3.6 molar solution of t-butyl hydroperoxide in toluene (375 mmol) is added dropwise at 28° C. within 2 hours. During this period, the temperature rises to 40° C. The solution is then held at 65° C. for 14 hours, and subsequently at 80° C. for another 2 hours. The reaction mixture is filtered over magnesium silicate, followed by washing with two 20 ml portions of toluene. The low-boiling components are stripped off on a rotary evaporator. The residue obtained is taken up in 50 ml of hexane and left to crystallize for 12 hours at −28° C. The resulting slurry of solids is filtered off with suction and dried at room temperature in an oil pump vacuum.

Yield: 96.7 g=73.2% of theory
Melting point: 72°–74° C.
Elementary analysis:

|  | C | H | F |
|---|---|---|---|
| calc. | 34.11 | 1.72 | 61.15 |
| obs. | 33.9 | 1.8 | 61.2 |

EXAMPLE 5

Preparation of 2,3-epoxy-5-(2,2,3,3,4,4,5,5,6,6,7,7,7-tridecafluoroheptyl)bicyclo[2.2.1]heptane 10.7 g (25 mmol) of the Diels-Alder product of 4,4,5,5,6,6,7,7,8,8,9,9,9-tridecafluoro-1-nonene (perfluorohexyl-1-propene) and cyclopentadiene are mixed in 10 ml of dry toluene with 326 mg (1 mmol) of molybdenum acetylacetonate, and 13 ml of a 2.9 molar solution of t-butyl hydroperoxide in toluene (37.5 mmol) are added dropwise at 22° C. within 30 minutes. During this period, the temperature rises to 60° C. The solution is then held at 60° C. for another 2 hours. The low-boiling components are distilled off under reduced pressure at 40° C., and the residue is chromatographed on silica gel. The mobile solvent used is a mixture of hexane/methylene chloride/diethyl ether (10:10:0.5 parts by volume). The product-containing fractions are combined. After the mobile solvent is distilled off, 7.3 g of a white solid remain behind.

Yield: 7.3 g = 66% of theory
Melting point: 39°–41° C.
Elementary analysis:

|  | C | H | F |
|---|---|---|---|
| calc. | 38.93 | 2.51 | 55.85 |
| obs. | 38.3 | 2.6 | 55.1 |

EXAMPLE 6

Preparation of 2,3-epoxy-5-(3,3,4,4,5,5,6,6,7,7,8,8,8-tridecafluorooctyl)bicyclo[2.2.1]heptane 4.4 g (10 mmol) of the Diels-Alder product of 5,5,6,6,7,7,8,8,9,9,10,10,10-tridecafluoro-1-decene (perfluorohexyl-1-butene) and cyclopentadiene are mixed in 10 ml of dry toluene with 133 mg (0.4 mmol) of molybdenum acetylacetonate, and 5.2 ml of a 2.9 molar solution of t-butyl hydroperoxide in toluene (1.5 mmol) are added dropwise at 22° C. within 15 minutes. During this time, the temperature rises to 31° C. The solution is then held at 60° C. for 17 hours. The solvent is then removed on a rotary evaporator at room temperature under reduced pressure. The residue is chromatographed on silica gel. The mobile solvent used is a mixture of hexane/methylene chloride/diethyl ether (10:10:0.5 parts by volume). The product-containing fractions are combined. After the mobile solvent has been distilled off, 2.0 g of a white solid remain behind.

Yield = 43% of theory.

We claim:

1. A fluorine-substituted epoxide of the formula

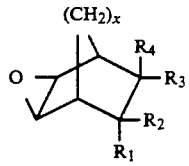

in which $R_1$ is an alkyl of the formula

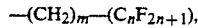

$-(CH_2)_m-(C_nF_{2n+1})$, in which m is 1 or 2, and n is an integer from 1 to 17, and x is 0 or 1 and $R_2$, $R_3$ and $R_4$ are the same or different and are radicals selected from the group consisting of H, fluorine, $C_1$ to $C_{18}$-alkyl, fluorine-substituted $C_1$ to $C_{18}$-alkyl and an alkyl of the formula

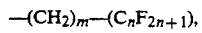

$-(CH_2)_m-(C_nF_{2n+1})$, in which m is 1 or 2, and n is an integer from 1 to 17.

2. A fluorine-substituted epoxide consisting of 2,3-epoxy-5,5-bis(trifluoromethyl)bicyclo[2.2.1]heptane.

3. A fluorine-substituted epoxide consisting of 2,3-epoxy-5-(perfluorohexyl)bicyclo[2.2.1]-heptane.

4. A fluorine-substituted epoxide consisting of 2,3-epoxy-5-(perfluorohexyl)bicyclo[2.2.1]-heptane.

5. A fluorine-substituted epoxide consisting of 1,2-epoxy-4-(perfluorohexyl)cyclohexane.

6. A fluorine-substituted epoxide consisting of 2,3-epoxy-5-(2,2,3,3,4,4,5,5,6,6,7,7,7-tridecafluoroheptyl)-bicyclo[2.2.1]-heptane.

7. A fluorine-substituted epoxide consisting of 2,3-epoxy-5-(3,3,4,4,5,5,6,6,7,7,8,8,8-tridecafluorooctyl)-bicyclo[2.2.1]-heptane.

* * * * *